(12) United States Patent
Saragovi et al.

(10) Patent No.: US 9,296,691 B2
(45) Date of Patent: Mar. 29, 2016

(54) INHIBITORS OF P75 RECEPTOR AND THEIR USES

(75) Inventors: Horacio Uri Saragovi, Montreal (CA); Hinyu Nedev, Laval (CA)

(73) Assignee: Horacio Uri Saragovi, Montreal (CA)

( * ) Notice: Subject to any disclaimer, the term of this patent is extended or adjusted under 35 U.S.C. 154(b) by 0 days.

(21) Appl. No.: 13/879,226

(22) PCT Filed: Oct. 13, 2011

(86) PCT No.: PCT/CA2011/001158
§ 371 (c)(1),
(2), (4) Date: Aug. 8, 2013

(87) PCT Pub. No.: WO2012/048417
PCT Pub. Date: Apr. 19, 2012

(65) Prior Publication Data
US 2013/0310404 A1    Nov. 21, 2013

Related U.S. Application Data

(60) Provisional application No. 61/392,647, filed on Oct. 13, 2010.

(51) Int. Cl.
*C07D 473/06*   (2006.01)
*C07D 473/08*   (2006.01)
*C07D 209/20*   (2006.01)
*C07D 209/18*   (2006.01)

(52) U.S. Cl.
CPC ............ *C07D 209/20* (2013.01); *C07D 209/18* (2013.01); *C07D 473/06* (2013.01); *C07D 473/08* (2013.01)

(58) Field of Classification Search
CPC ........................... C07D 473/08; C07D 473/04
See application file for complete search history.

(56) References Cited

U.S. PATENT DOCUMENTS

2007/0219222 A1 *  9/2007  Moran et al. ............. 514/263.35

FOREIGN PATENT DOCUMENTS

| CA | 2 634 152 | 6/2007 |
| CA | 2634152 A1 * | 6/2007 |
| WO | WO 2010/036821 | 4/2010 |
| WO | WO 2010/102212 A2 | 9/2010 |

OTHER PUBLICATIONS

Tsvetkova et al., "Esterification of 7-Theophyllineacetic acid with Dlethylene Glycol Monomethyl Ether", Acta Pharm, 2006, pp. 251-257, vol. 56.
Brunet et al., "Several; Derivatives of Rgeophylline-7-acetic acid", Bulletin de la Societe Chimique de France, 1996, pp. 1333-1335.

* cited by examiner

*Primary Examiner* — Golam M M Shameem
*Assistant Examiner* — Laura Daniel
(74) *Attorney, Agent, or Firm* — Norton Rose Fulbright Canada

(57) ABSTRACT

Novel p75 receptor antagonist compounds and compositions and uses thereof for the prevention and treatment of p75-associated disorders, such as neurodegenerative diseases, are described.

5 Claims, 3 Drawing Sheets

INHIBITORS OF P75 RECEPTOR AND THEIR USES

FIELD OF THE INVENTION

This invention relates to novel p75 receptor antagonist compounds and compositions and uses thereof for the prevention and treatment of p75-associated disorders, such as neurodegenerative diseases.

BACKGROUND

The neurotrophins, including nerve growth factor (NGF), brain derived neurotrophic factor (BDNF), neurotrophin 3 (NT-3), and neurotrophin 4/5 (NT-4/5), are among the molecular determinants that regulate the generation of diverse cell populations, especially neuronal cells and the maintenance of their functions within the nervous system, and many other cell types.

Neurotrophins are synthesized as precursors, called proneurotrophins, that are processed by proteolytic cleavage into their mature forms. The interaction of pro-neurotrophins with their receptors results in activation of death-pathways in many cell types.

In addition to regulating the life, function and/or death of neurons, the neurotrophins and pro-neurotrophins also regulate the development and viability of non-neuronal cell populations in skin, vascular endothelium, vascular pericytes, hair follicles, corneal epithelium, gut epithelium, retinal cells, glial cells, astrocytes, lymphocytes, and others. Neurotrophins and pro-neurotrophins have also been implicated or associated with several forms of cancer such as neuroblastoma, medulloblastoma, breast cancer, prostate cancer, and others.

All the mature neurotrophins and the pro-neurotrophins interact with the p75 receptor, a promiscuous receptor which binds to these 8 ligands (the 4 mature neurotrophins and their corresponding pro-neurotrophins). The p75 receptor belongs to the tumor necrosis factor (TNF) receptor superfamily. Neurotrophin binding takes place at the extracellular domain of p75, reportedly at the third and fourth cysteine loops.

The mature neurotrophins also bind more specifically to a receptor tyrosine kinase, called Trk (i.e., NGF binds to TrkA, BDNF and NT-4/5 bind to TrkB, and NT-3 binds to TrkC). These interactions trigger a cascade of known signals in the cell.

The TrkA, TrkB and TrkC receptors are expressed in neuroblastoma, medulloblastoma, breast cancer, prostate cancer, lymphoma, and other types of cancer cells.

In the CNS, cholinergic neurons express TrkA, dopaminergic neurons express TrkB, and retinal ganglion cells express TrkA and TrkB. In the PNS, motor neurons express TrkC, and sensory neurons express TrkA. Most of these neuronal populations also express the p75 receptor (also referred to as "p75"). Co-expression of p75 and a trk receptor on the same cell causes a "cross-talk" between the receptors; that is, there is a functional cross-regulation of one receptor upon the other. The cross-talk depends on the ligands engaging each receptor, and on the relative ratio of each receptor expressed on the cell surface.

Besides cells co-expressing both receptors or Trk receptors alone, there are many cell types that express p75, such as skin, vascular endothelium, vascular pericytes, hair follicles, corneal epithelium, gut epithelium, and pigmented epithelium; retinal cells such as glial cells, Muller cells, and photoreceptor cells; brain cells such as neurons, astrocytes and glia; and also lymphocytes and other cell types.

There is a need for novel inhibitors of p75 receptor function and/or activation which can be used therapeutically for p75-associated disorders or conditions.

SUMMARY OF THE INVENTION

We report herein novel compounds and compositions thereof which have binding specificity for a p75$^{NTR}$ receptor molecule and are useful therefore in the treatment and prevention of diseases or conditions characterized by p75 activation, such as neurodegenerative disorders.

In accordance with the present invention, there are provided novel compounds of Formulae I, Ia, Ib, II, IIa, IIb and Table 1, as set forth in detail below, as well as pharmaceutically acceptable salts thereof. Pharmaceutical compositions comprising the compounds described herein and a pharmaceutically acceptable carrier are also provided.

Further in accordance with the present invention, there is provided a method for inhibiting p75 receptor in a subject, comprising administering the compounds and compositions described herein to the subject, such that p75 receptor is inhibited in the subject. In one aspect, p75 receptor activation is inhibited in said subject. In another aspect, p75 receptor function is inhibited in said subject.

There is also provided herein a method for preventing or treating a disease or condition characterized by p75 activation in a subject, comprising administering an effective amount of the compounds and compositions described herein to the subject.

In one embodiment, the disease or condition which is prevented or treated is a neurodegenerative disease. For example, the neurodegenerative disease may be Alzheimer's disease, Down's syndrome, Creutzfeldt-Jacob disease, kuru, scrapie, transmissible mink encephalopathy, Huntington's disease, Riley-Day familial dysautonomia, multiple system atrophy, amyotrophic lateral sclerosis (ALS), glaucoma, macular degeneration, neuropathy, ischemia, hypoxia, neural injury, epilepsy, Parkinson's disease, spinal cord injury or neuroblastoma. In an embodiment, the death of hair follicles is prevented in the subject. In another embodiment, the neurodegenerative disease is a disease which can be treated with agents that activate a Trk receptor, or with neurotrophins such as NGF, or neurotrophin-derived peptides or peptidomimetics.

In a particular aspect, there is provided a compound of Formula I:

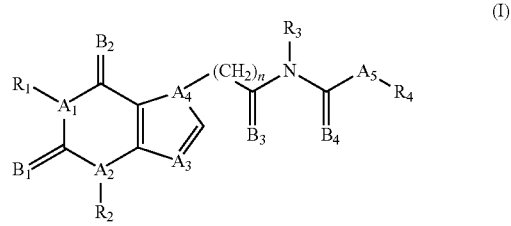

(I)

wherein: $A_1$, $A_2$, $A_3$, $A_4$ and $A_5$ are each independently selected from the group consisting of H, N, NH, $CH_2O$ and S; $B_1$, $B_2$, $B_3$ and $B_4$ are each independently selected from the group consisting of O, S, and H; $R_1$ and $R_2$ are each independently selected from the group consisting of H, alkyl, substituted alkyl, cycloalkyl, aryl, and substituted aryl; $R_3$ and $R_4$ are each independently selected from the group consisting of H, alkyl, isoalkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl and alkoxycarbonyl; and n is an integer from 0 to 8; or a pharmaceutically acceptable salt thereof.

In another aspect, there is provided a compound of Formula I, the compound having the following structure (Ia):

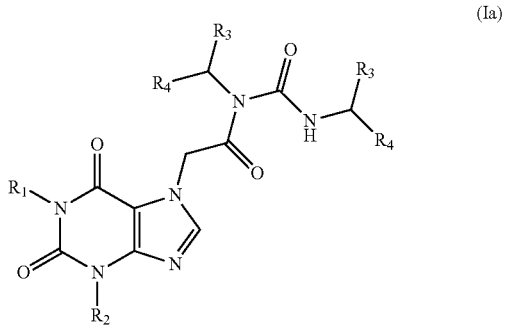

(Ia)

wherein: $R_1$ and $R_2$ are each independently selected from the group consisting of H, alkyl, substituted alkyl, cycloalkyl, aryl, substituted aryl, aralkyl and aralkyloxyl; and $R_3$ and $R_4$ are each independently selected from the group consisting of H, alkyl, isoalkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl and alkoxycarbonyl; or a pharmaceutically acceptable salt thereof.

In a further aspect, there is provided a compound of Formula I, the compound having the following structure (Ib):

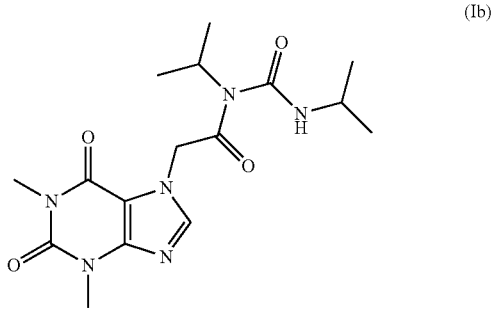 [SMILES: CC(C)NC(=O)N(C(=O)Cn1cnc2c1c(=O)n(C)c(=O)n2C)C(C)C]

(Ib)

or a pharmaceutically acceptable salt thereof.

In yet another aspect, there is provided a compound of Formula (II):

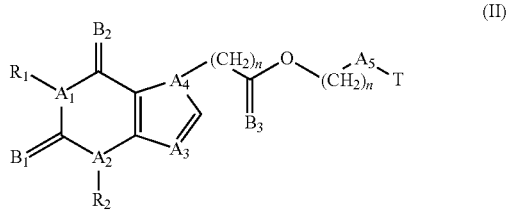

(II)

wherein: $A_1$, $A_2$, $A_3$, $A_4$ and $A_5$ are each independently selected from the group consisting of NH, $CH_2O$ and S; $B_1$, $B_2$, and $B_3$ are each independently selected from the group consisting of O and S; $R_1$ and $R_2$ are each independently selected from the group consisting of H, alkyl, substituted alkyl, cycloalkyl, aryl, and substituted aryl; T is an amino-protecting group selected from the group consisting of benzyloxycarbonyl, t-butyloxycarbonyl, p-methoxybenzyloxycarbonyl, 2-chlorobenzyloxycarbonyl, p-toluenesulfonyl, trifluoroacetyl, phthalyl, formyl, o-nitrophenylsulfenyl, 3-nitro-2-pyridinesulfenyl, fluorenyl and hydrogen; and n is an integer from 0 to 8; or a pharmaceutically acceptable salt thereof.

In another aspect, there is provided a compound having the following structure (IIa):

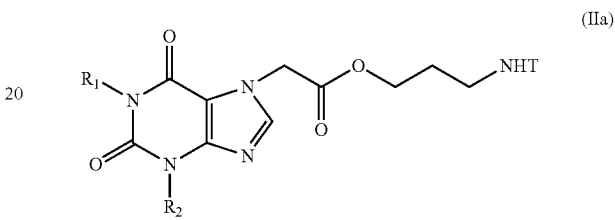

(IIa)

wherein: $R_1$ and $R_2$ are each independently selected from the group consisting of H, alkyl, substituted alkyl, cycloalkyl, aryl, substituted aryl, aralkyl, and aralkyloxyl; and T is an amino-protecting group selected from the group consisting of benzyloxycarbonyl, t-butyloxycarbonyl, p-methoxybenzyloxycarbonyl, 2-chlorobenzyloxycarbonyl, p-toluenesulfonyl, trifluomacetyl, phthalyl, formyl, o-nitrophenylsulfenyl, 3-nitro-2-pyridinesulfenyl, fluorenyl and hydrogen; or a pharmaceutically acceptable salt thereof.

In a still further aspect, there is provided a compound having the following structure (IIb):

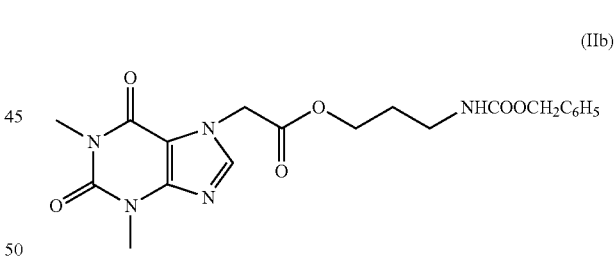

(IIb)

or a pharmaceutically acceptable salt thereof.

In another aspect, there is provided a compound selected from the group consisting of:

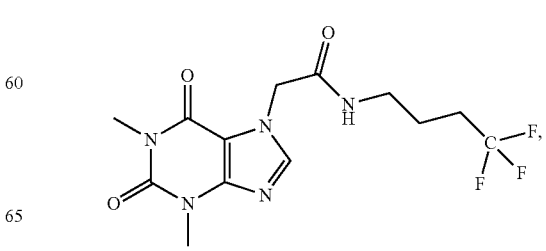

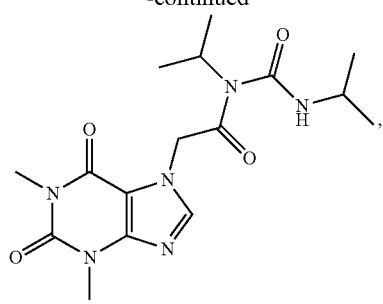
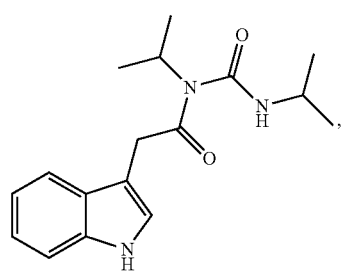
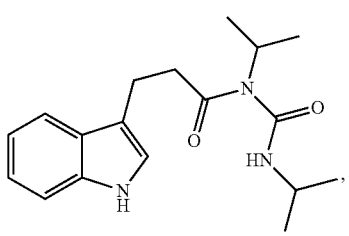
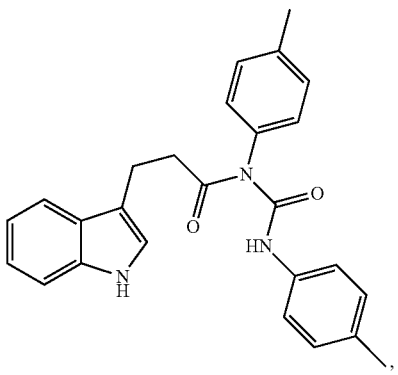
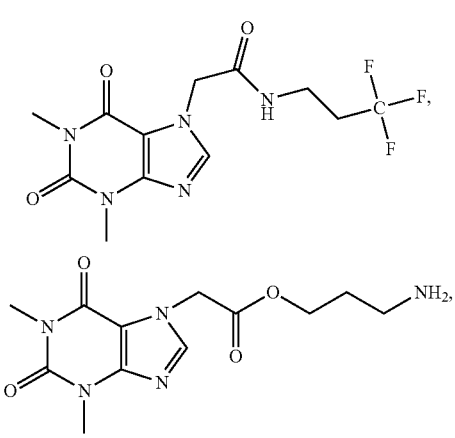
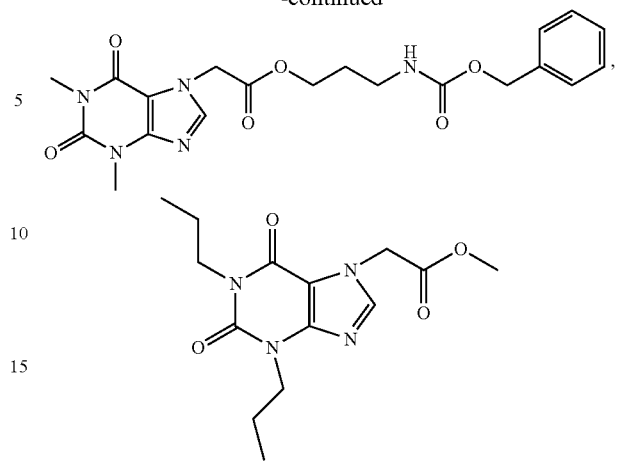

and pharmaceutically acceptable salts thereof.

Pharmaceutical compositions comprising the compounds described herein and a pharmaceutically acceptable carrier are also provided.

In another aspect, there are provided methods for inhibiting p75 receptor in a subject comprising administering the compounds and compositions described herein, such that p75 receptor is inhibited in said subject. In one aspect, p75 receptor activation is inhibited in said subject. In another aspect, p75 receptor function is inhibited in said subject.

In yet another aspect, there are provided methods for preventing or treating a disease or condition characterized by p75 activation in a subject, comprising administering an effective amount of the compounds or compositions described herein to the subject. In an aspect, p75 receptor activation is inhibited in said subject. In another aspect, p75 receptor function is inhibited in said subject.

In a further aspect, the disease or condition to be treated or prevented is a neurodegenerative disease. For example, the neurodegenerative disease may be Alzheimer's disease, Down's syndrome, Creutzfeldt-Jacob disease, kuru, scrapie, transmissible mink encephalopathy, Riley-Day familial dysautonomia, multiple system atrophy, amyotrophic lateral sclerosis (ALS), glaucoma, neuropathy, ischemia, hypoxia, neural injury, Huntington's disease, epilepsy, Parkinson's disease, spinal cord injury or neuroblastoma. In one aspect, the neurodegenerative disease is a disease which can be treated with agents that activate a Trk receptor, with neurotrophins, and/or with neurotrophin-derived peptides or peptidomimetics. The neurotrophin may be, for example, NGF.

In one aspect, the death of hair follicles is prevented in the subject.

DETAILED DESCRIPTION

Figure 1:
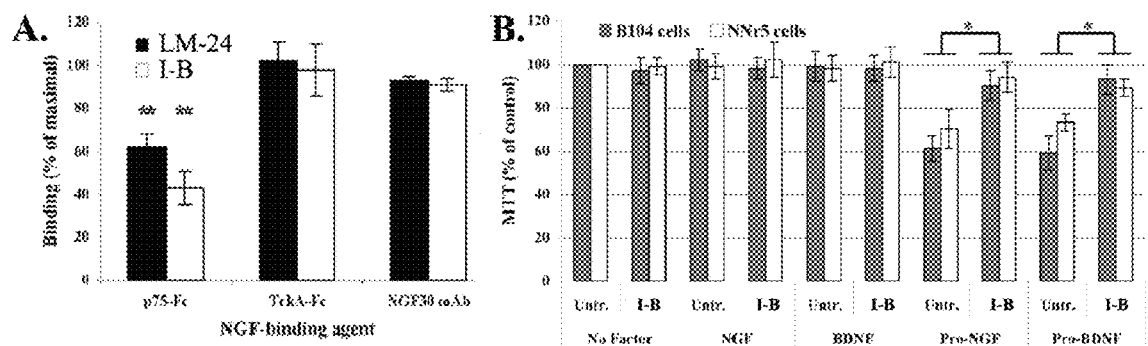
FIG. 1 shows that compound I-B inhibits NGF-p75 binding selectively, and inhibits the pro-NGF killing function. (A) shows a characterization of p75 antagonists I-B and LM-24. Wild type NGF was immobilized on ELISA plates and binding of the indicated primary reagents [p75-Fc (n=5), TrkA-Fc (n=4), or anti-NGF mAb NGF30 (n=3)] was tested at 50 nM final concentrations. Binding was revealed with HRP-labeled anti-Fc secondary reagents. Untreated wells were standardized to 100%. LM-24 or I-B (each at 30 μM) inhibited the binding of NGF.p75 selectively, and did not inhibit NGF.TrkA or NGF.NGF30 binding. Data shown is % inhibition ±sem, of the indicated number (n) of assays, each assay in triplicate, **p<0.01. Shown are the chemical structures of I-B and LM-24. In (B), B104 (gray bars) and nnr5 cells (white bars) were cultured in serum-containing media, supplemented with the indicated growth factor (50 nM) ±I-B (20 µM). MTT data were standardized to untreated control ±SD, n=4 replicates. *p<0.05. Similar data were obtained in 2 independent experiments where pro-NTFs had a deleterious effect.

There are provided herein novel compounds and compositions thereof having binding specificity for a p75$^{NTR}$ receptor molecule. These compounds and compositions are useful in the treatment and prevention of diseases or conditions characterized by p75 activation, such as neurodegenerative disorders. Methods of treating or preventing such diseases or conditions using the compounds and compounds of the invention are also provided.

In one embodiment, there is provided herein a compound of Formula (I):

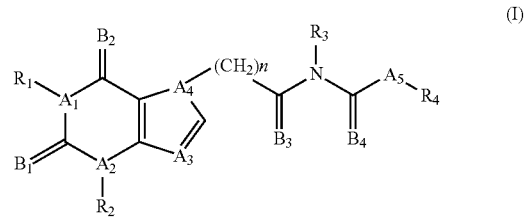

(I)

wherein:

$A_1$, $A_2$, $A_3$, $A_4$ and $A_5$ are each independently selected from the group consisting of H, N, NH, $CH_2O$ and S;

$B_1$, $B_2$, $B_3$ and $B_4$ are each independently selected from the group consisting of O, S, H and $NR_5$, wherein $R_5$ is selected from the group consisting of H, alkyl, substituted alkyl, cycloalkyl, aryl and substituted aryl;

$R_1$ and $R_2$ are each independently selected from the group consisting of H, alkyl, substituted alkyl, cycloalkyl, aryl, and substituted aryl;

$R_3$ and $R_4$ are each independently selected from the group consisting of H, alkyl, isoalkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl and alkoxycarbonyl; and n is an integer from 0 to 8.

In another embodiment, there is provided herein a compound of Formula (I):

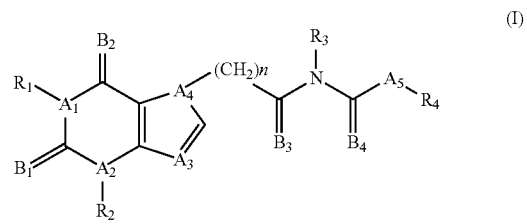

(I)

wherein:

$A_1$, $A_2$, $A_3$, $A_4$ and $A_5$ are each independently selected from the group consisting of H, N, NH, $CH_2O$ and S;

$B_1$, $B_2$, $B_3$ and $B_4$ are each independently selected from the group consisting of O, S and H;

$R_1$ and $R_2$ are each independently selected from the group consisting of H, alkyl, substituted alkyl, cycloalkyl, aryl, and substituted aryl;

$R_3$ and $R_4$ are each independently selected from the group consisting of H, alkyl, isoalkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl and alkoxycarbonyl; and n is an integer from 0 to 8.

It will be appreciated that when $B_1$, $B_2$, $B_3$ and $B_4$ are H, there is an aromatic resonance structure, due to the double bond in the ring.

In an embodiment, the compound of Formula (I) has the following structure (Ia):

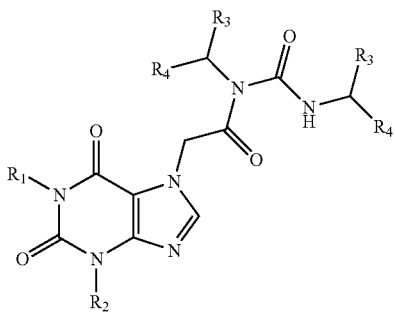

wherein:
$R_1$ and $R_2$ are each independently selected from the group consisting of H, alkyl, substituted alkyl, cycloalkyl, aryl, substituted aryl, aralkyl and aralkyloxyl; and
$R_3$ and $R_4$ are each independently selected from the group consisting of H, alkyl, isoalkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl and alkoxycarbonyl.

In another embodiment, the compound of Formula (I) has the following structure (Ib):

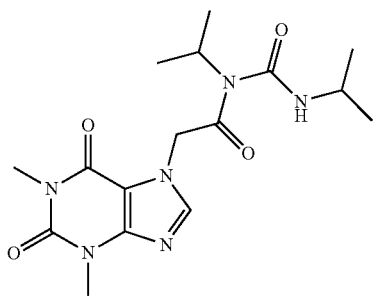

In one embodiment, there is provided a compound of Formula (II):

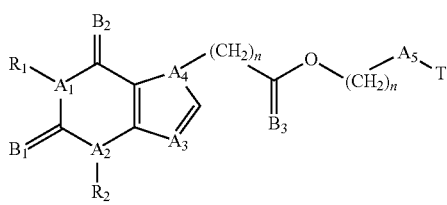

wherein:
$A_1$, $A_2$, $A_3$, $A_4$ and $A_5$ are each independently selected from the group consisting of NH, $CH_2O$ and S;
$B_1$, $B_2$, and $B_3$ are each independently selected from the group consisting of O, S, and $NR_5$, wherein $R_5$ is selected from the group consisting of H, alkyl, substituted alkyl, cycloalkyl, aryl and substituted aryl;
$R_1$ and $R_2$ are each independently selected from the group consisting of H, alkyl, substituted alkyl, cycloalkyl, aryl, and substituted aryl;

T is an amino-protecting group selected from the group consisting of benzyloxycarbonyl, t-butyloxycarbonyl, p-methoxybenzyloxycarbonyl, 2-chloro-benzyloxycarbonyl, p-toluenesulfonyl, trifluoroacetyl, phthalyl, formyl, o-nitrophenylsulfenyl, 3-nitro-2-pyridinesulfenyl, fluorenyl and hydrogen; and n is an integer from 0 to 8. In another embodiment, there is provided a compound of Formula (II):

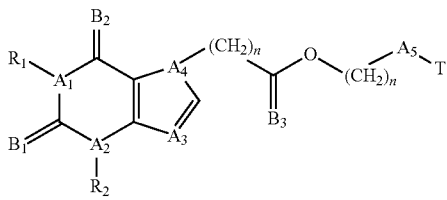

wherein:
$A_1$, $A_2$, $A_3$, $A_4$ and $A_5$ are each independently selected from the group consisting of NH, $CH_2O$ and S;
$B_1$, $B_2$, and $B_3$ are each independently selected from the group consisting of O and S;
$R_1$ and $R_2$ are each independently selected from the group consisting of H, alkyl, substituted alkyl, cycloalkyl, aryl, and substituted aryl;

T is an amino-protecting group selected from the group consisting of benzyloxycarbonyl, t-butyloxycarbonyl, p-methoxybenzyloxycarbonyl, 2-chloro-benzyloxycarbonyl, p-toluenesulfonyl, trifluoroacetyl, phthalyl, formyl, o-nitrophenylsulfenyl, 3-nitro-2-pyridinesulfenyl, fluorenyl and hydrogen; and n is an integer from 0 to 8.

In an embodiment, the compound of Formula (II) has the following structure (IIa):

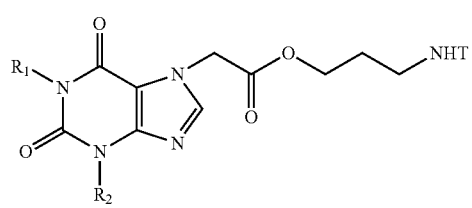

wherein:
$R_1$ and $R_2$ are each independently selected from the group consisting of H, alkyl, substituted alkyl, cycloalkyl, aryl, substituted aryl, aralkyl, and aralkyloxyl; and T is an amino-protecting group selected from the group consisting of benzyloxycarbonyl, t-butyloxycarbonyl, p-methoxybenzyloxycarbonyl, 2-chlorobenzyloxycarbonyl, p-toluenesulfonyl, trifluomacetyl, phthalyl, formyl, o-nitrophenylsulfenyl, 3-nitro-2-pyridinesulfenyl, fluorenyl and hydrogen.

In another embodiment, the compound of Formula (II) has the following structure (IIb):

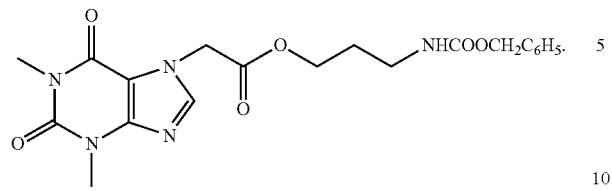
(IIb)
In an embodiment, there are provided the novel compounds of Table 1:
TABLE 1
Compounds
| Code Name | Structure |
|---|---|
| I-A (Th53) | 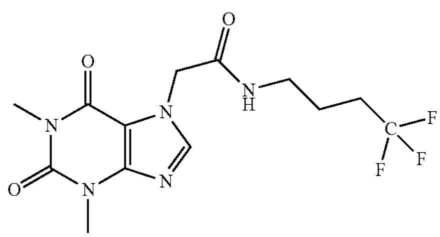 [SMILES: Cn1c(=O)c2c(ncn2CC(=O)NCCCC(F)(F)F)n(C)c1=O] |
| I-B (Th69) | 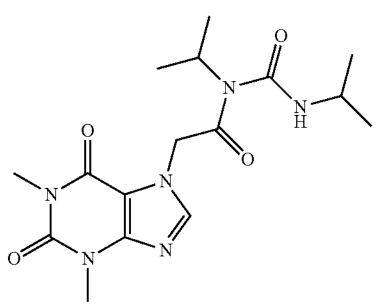 [SMILES: CC(C)NC(=O)N(C(=O)Cn1cnc2c1c(=O)n(C)c(=O)n2C)C(C)C] |
| I-F (Th70-2) | 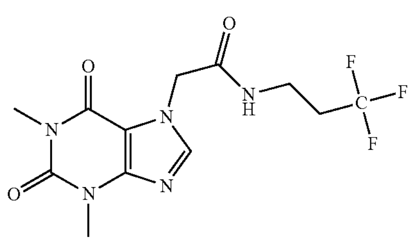 [SMILES: Cn1c(=O)c2c(ncn2CC(=O)NCCC(F)(F)F)n(C)c1=O] |
| I-Q (Th92) | 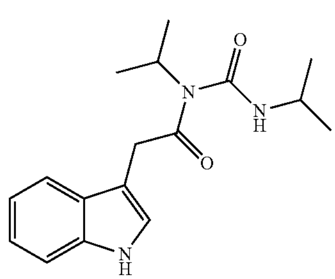 [SMILES: CC(C)NC(=O)N(C(=O)Cc1c[nH]c2ccccc12)C(C)C] |

TABLE 1-continued
Compounds
| Code Name | Structure |
|---|---|
| I-R (Th93) | 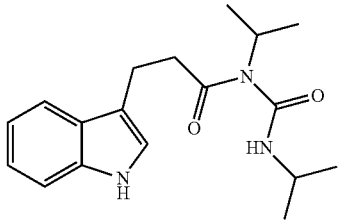 [SMILES: CC(C)NC(=O)N(C(=O)CCc1c[nH]c2ccccc12)C(C)C] |
| I-S (Th95) | 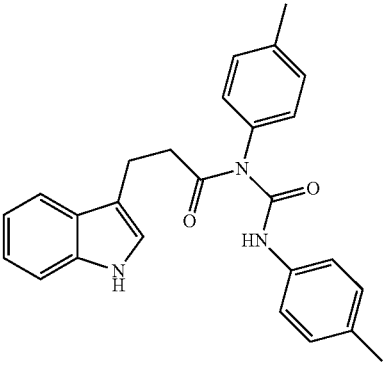 [SMILES: Cc1ccc(NC(=O)N(C(=O)CCc2c[nH]c3ccccc23)c2ccc(C)cc2)cc1] |
| II-D (Th60) | 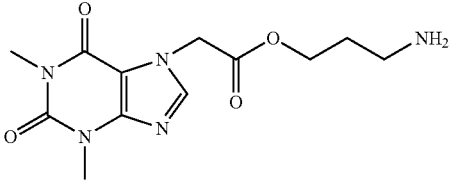 [SMILES: Cn1c(=O)c2c(ncn2CC(=O)OCCCN)n(C)c1=O] |
| II-E (Th56) | 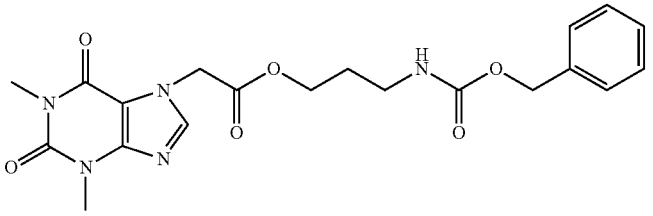 [SMILES: Cn1c(=O)c2c(ncn2CC(=O)OCCCNC(=O)OCc2ccccc2)n(C)c1=O] |
| II-N (TH86) | 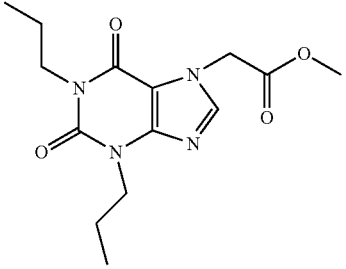 [SMILES: CCCn1c(=O)c2c(ncn2CC(=O)OC)n(CCC)c1=O] |

In another embodiment, there is provided the novel use of the compounds of Table 1 and 2 for prevention or treatment of a disease or condition characterized by p75 activation, such as a neurodegenerative disorder.

TABLE 2

| Code Name | Structure |
|---|---|
| I-G[a] (Th41) | (structure) |
| II-H[a] (Th75) | (structure) |

[a]Klosa, J. (1955) Archly der Pharmazie and Berichte der Deutschen Pharmazeutischen Gesellschaft 288: 301-303; Peikov, P., et al., (1995) Archly der Pharmazie 328: 615-618.

In another embodiment, there is provided the novel use of the p75 antagonist compound of Table 3 for prevention or treatment of a disease or condition characterized by p75 activation, such as a neurodegenerative disorder:

TABLE 3

| Code Name | Structure |
|---|---|
| LM-24[b] | (structure) |

[b]Massa, S.M., et al. (2006) J. Neurosci. 26: 5288-5300.

It should be understood that references to the compounds of the invention described herein are meant to also include the pharmaceutically acceptable salts as well as acidic and basic forms of the compounds.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

Pharmaceutical compositions are also provided herein. The pharmaceutical compositions of the invention comprise the p75 receptor antagonist compounds described herein, e.g. a compound of Formula I, Ia, Ib II, IIa, or IIb, or a compound of Table 1, 2, or 3, or a pharmaceutically acceptable salt thereof, as an active ingredient, and may also contain a pharmaceutically acceptable carrier.

Any suitable route of administration may be employed for providing a mammal, especially a human with an effective dosage of a compound or composition of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of the invention in suitable propellants, such as fluorocarbons or hydrocarbons.

Suitable topical formulations of the compounds and compositions of the invention include transdermal devices, aerosols, creams, ointments, lotions, dusting powders, and the like.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations' such as, for example, suspensions, elixirs and solutions; or carriers such as starches, sugars, microcrystalline cellulose, diluents, granulating agents, lubricants, binders, disintegrating agents and the like in the case of oral solid preparations; such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or non-aqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. For example, in an embodiment each tablet may contain from about 2.5 mg to about 500 mg of the active ingredient and each cachet or capsule may contain from about 2.5 to about 500 mg of the active ingredient.

The magnitude of prophylactic or therapeutic dose of a compound of the invention will, of course, vary with the nature of the severity of the condition to be treated and with the particular compound of the invention and its route of administration. It will also vary according to the age, weight and response of the individual patient. In general, the daily dose range may lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, in an embodiment a suitable dosage range may be from about 0.001 mg to about 25 mg (preferably from 0.01 mg to about 1 mg) of a compound of the invention per kg of body weight per day.

In the case where an oral composition is employed, in an embodiment a suitable dosage range may be, e.g. from about 0.01 mg to about 100 mg of a compound of the invention per kg of body weight per day, preferably from about 0.1 mg to about 10 mg per kg.

For the treatment of diseases of the eye, ophthalmic preparations for ocular administration comprising 0.001-1% by weight solutions or suspensions of the compounds of the invention in an acceptable ophthalmic formulation may be used in an embodiment.

The compounds and compositions described herein are p75 receptor antagonists and, accordingly, can be used to treat or prevent any disease, disorder or condition in which p75 receptor expression or activity is deleterious. For example, p75 receptor induced cell death (i.e. apoptosis) can be inhibited using the compounds and compositions described herein.

It is noted that, since compounds of the invention are much smaller in size than NGF, they are therefore more amenable to passing blood-tissue barriers when desired and are less likely to elicit an adverse immunological response. Thus, in an aspect, the compounds and compositions described herein may be used to treat conditions or disorders, including degenerative and other disorders of the nervous system, which respond to treatment with agents that activate a Trk receptor, with neurotrophins such as NGF, and/or with neurotrophin-derived peptides or peptidomimetics.

In an embodiment, methods for treating or preventing a disease or condition characterized by p75 activation comprising administering a compound or composition of the invention to a subject in need thereof are provided herein. In another embodiment, there is provided a method for preventing or treating conditions involving degeneration or dysfunction of cells expressing p75 receptor.

In another embodiment, there are provided methods for treating or preventing a neurodegenerative disorder, comprising administering a compound or composition of the invention to a subject in need thereof. In an embodiment, the neurodegenerative disorder is selected from the group consisting of Parkinson's disease, Alzheimer's disease, Huntington's disease, amyotrophic lateral sclerosis (ALS), epilepsy, Pick's disease, stroke, hypoxia, spinal cord injury, hair loss, and other neurodegenerative conditions involving degeneration or dysfunction of cells expressing p75.

Thus, in an embodiment the compounds and compositions provided herein can be used to promote the growth and/or stimulate the survival of cells of the nervous system, including, but not limited to, dopaminergic neurons, cholinergic neurons, sensory neurons, striatal cells, cells of the cortex, striatum, hippocampus, cerebellum, olfactory bulbs, peraqueductal gray, raphe nuclei, locus coeruleus, dorsal root ganglion, neural placode derivatives, sympathetic neurons and lower motor neurons, photoreceptors, and retinal ganglion cells. The compounds and compositions provided herein can also be used to control the formation of neo-vasculature in conditions such as macular degeneration or diabetic retinopathy. In addition, the compounds and compositions of the invention can be used to control the growth or metastasis of tumors expressing p75 receptor. In an aspect, the compounds and compositions provided herein can be used to prevent or inhibit the death of hair follicles.

It should be understood that neurodegenerative disorder refers to a disease state in a mammal which can include degenerative growth and disorder of the nervous system and which, at least in some cases, can respond to treatment with agents that activate a Trk receptor, with neurotrophins such as NGF, and/or with neurotrophin-derived peptides or peptidomimetics. Thus, diseases characterized by the loss of function and or/degeneration of neurons and nerves are within the scope of this invention. In addition, any disease that can respond to NGF-responsive cells is within the scope of the present invention. Exemplary disorders include, without limitation, Alzheimer's disease, Down's syndrome, Creutzfeldt-Jacob disease, kuru, scrapie, transmissible mink encephalopathy, Huntington's disease, apoptosis, Riley-Day familial dysautonomia, multiple system atrophy, neuropathies, amyotrophic lateral sclerosis (ALS), glaucoma, ischemia, hypoxia, neural injury, epilepsy, Parkinson's disease, spinal cord injury, and the like. Additionally, tumors such as neuroblastomas may also be treated or prevented using the compounds and compositions of the invention.

In one embodiment, the disease, condition or disorder being treated or prevented is characterized by death of retinal ganglion cells (RGCs). For example, the disease may be glaucoma or macular degeneration. In another embodiment, RGC cell death is prevented or inhibited in the subject.

Neuropathic diseases of the retina that involve the death of the retinal ganglion cells (RGCs) are irreversible. This is because RGCs are neurons whose fibers and axons make up the optic nerve (ON) and relay visual input from the retina to the cerebral cortex. Commonly used animal models of neuropathy that cause RGC death include ON axotomy and glaucoma. ON axotomy is an acute model of trauma where the optic nerve is completely severed, causing the rapid death of the RGCs (~90% within 2 weeks). Glaucoma is a chronic and progressive optic nerve neuropathy often concomitant with elevated intraocular pressure (IOP). The etiology of RGC death in glaucoma remains unknown.

One mechanism may be the deprivation of survival signals that neurotrophins provide by acting through the TrkA and TrkB receptors expressed on RGCs. Indeed, activation of TrkA (Shi et al., 2007) or TrkB (Bai et al., 2010a) directly activates pro-survival signals during glaucoma and rescues RGCs from death during ON axotomy or glaucoma. However, it seems paradoxical that while TrkA activity is protective, neither endogenous nerve growth factor (NGF) (up-regulated in glaucoma (Rudzinski et al., 2004)) nor exogenous NGF protein applied as a drug afford effective RGC neuroprotection during ON axotomy or glaucoma (Lebrun-Julien et al., 2009b; Shi et al., 2007).

A second mechanism of RGC death in glaucoma is the increased production of tumor necrosis factor-α (TNF-α (Nakazawa et al., 2006; Tezel and Wax, 2004; Wax and Tezel, 2002) and α2-macroglobulin (α2M) (Shi et al., 2008). These neurotoxic factors are produced by activated microglia (Bai et al., 2010b), which express the neurotrophin receptor $p75^{NTR}$ (Lebrun-Julien et al., 2009b). Indeed, the $p75^{NTR}$ receptor has been implicated in the acute release of TNF-α during acute toxicity leading to RGC death within a few hours after intravitreal injection of glutamate (Lebrun-Julien et al., 2009a) or after activation by pro-NGF (Lebrun-Julien et al., 2010).

However, $p75^{NTR}$ is present in the normal retina, as well as many of its ligands (the mature and the precursor neurotrophins). Thus it is not clear what homeostatic balance keeps the normal adult retina from degenerating. In addition, the actual role of $p75^{NTR}$ in retinal disease states is not known. For example, a ligand such as NGF can bind to TrkA and to $p75^{NTR}$, signals that can be beneficial or deleterious. This complexity is especially important in disease states in which neurotrophic approaches have been attempted to prevent neuronal death.

Here, we show the role of $p75^{NTR}$ in retinal disease states using models of chronic neurodegeneration (glaucoma) or acute neurodegeneration (optic nerve axotomy). We show that inhibition of $p75^{NTR}$ is protective and prevents RGC death in both models of degeneration. One mechanism of protection is by reduction of the deleterious toxicity caused by TNF-α and α2M proteins. We show that antagonists of $p75^{NTR}$ significantly normalize production of these neurotoxic proteins.

As used herein, "subject" includes mammals, including humans.

In an embodiment, the methods disclosed herein comprise administration of a therapeutically effective amount of a compound or composition of the invention, to a subject in need thereof. A subject "in need thereof" is a subject suffering from or susceptible to the disease or condition in question. The term "therapeutically effective amount" refers to an amount of a compound which confers a therapeutic effect on the treated subject. The effect may be objective (i.e. measurable by some test or marker) or subjective (i.e. the subject gives an indication of or feels an effect). The term "effective amount" refers to an amount of a compound which is sufficient to produce the desired result or has the desired biological effect.

Use of the compounds of the invention in the manufacture of a medicament for treating the diseases disclosed herein are also encompassed, as are compositions for use for treating or preventing the described diseases.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Binding Assays

The effect of compounds I-B and LM-24 on the binding between NGF and p75 was tested in competitive ELISA assays, where the antagonists prevent soluble p75 from binding to immobilized NGF. The selectivity of antagonism was evaluated by lack of effect upon NGF-TrkA or lack of effect between NGF and anti-NGF monoclonal antibody (mAb) NGF30 interactions (FIG. 1A).

I-B and LM-24 antagonized NGF-p75NTR interactions selectively. In controls, they did not interfere with the binding of TrkA to NGF or mAb NGF30 binding to NGF (FIG. 1A). The use of mAb NGF30 is an ideal control, because the mAb is known to recognize a p75NTR binding domain of NGF. Similar data were obtained in ELISA assays where pro-NGF was immobilized (data not shown). These data show that the compounds bind to p75, and prevent p75 binding to NGF or to pro-NGF.

Results from similar competitive ELISA assays using the compounds of the present invention are shown in Table 4.

TABLE 4

Summary of ELISA binding data described for FIG. 1A. Each independent assay (n) was done in triplicate or quadruplicate. Binding to levels significantly lower than 100% indicates inhibition.

|  | No cpd | I-A | I-B | I-F | I-G | I-Q | I-R | I-S | II-D | II-E | II-H | II-N |
|---|---|---|---|---|---|---|---|---|---|---|---|---|
| p75-Fc binding |  |  |  |  |  |  |  |  |  |  |  |  |
| AVERAGE | 100 | 74 | 52 | 73 | 62 | 53 | 59 | 56 | 69 | 56 | 72 | 83 |
| Indep. Assays (n) | 5 | 5 | 8 | 3 | 3 | 2 | 2 | 2 | 5 | 5 | 3 | 2 |
| SD | 0 | 11 | 9 | 9 | 5 | 11 | 14 | 14 | 7 | 10 | 9 | 5 |

TABLE 4-continued

Summary of ELISA binding data described for FIG. 1A. Each independent assay (n) was done in triplicate or quadruplicate. Binding to levels significantly lower than 100% indicates inhibition.

|  | No cpd | I-A | I-B | I-F | I-G | I-Q | I-R | I-S | II-D | II-E | II-H | II-N |
|---|---|---|---|---|---|---|---|---|---|---|---|---|
| TrkA-Fc binding | | | | | | | | | | | | |
| AVERAGE | 100 | 105 | 107 | 91 | 99 | | | | 116 | 94 | 94 | |
| Indep. Assays (n) | 4 | 4 | 7 | 3 | 3 | | | | 4 | 4 | 3 | |
| SD | 0 | 8 | 8 | 3 | 19 | | | | 15 | 5 | 10 | |
| NGF30 binding | | | | | | | | | | | | |
| AVERAGE | 100 | 86 | 88 | | | | | | 91 | 89 | | |
| Indep. Assays (n) | 2 | 2 | 2 | | | | | | 2 | 2 | | |
| SEM | 0 | 5 | 6 | | | | | | 0 | 3 | | |

EX VIVO Biological Assays

The effect of I-B on the pro-apoptotic function of pro-NGF or pro-BDNF was tested in functional MTT assays measuring cell metabolism (FIG. 1B). Pro-NGF and pro-BDNF significantly (p<0.05) reduced the viability of B104 cells (~50,000 p75NTR per cell) or nnr5 cells (~200,000 p75NTR per cell). Addition of I-B in these conditions prevented the loss of cell viability, indicating functional antagonism of pro-NTF-p75NTR.

IN VIVO Neuroprotection Assays

To study p75NTR as a pharmacological target, we tested antagonists of this receptor in ON axotomy and in glaucoma.

Antagonists of p75NTR prevented loss of retinal structure after ON axotomy. The relative in vivo efficacy for I-B and LM-24 was tested using the ON axotomy model. A quantitative non-invasive structural endpoint, FD-OCT, was performed in the same animal over time to measure the integrity of the neuronal layers. We quantified the axons and fibers of the RGCs that contribute to the thickness of the Nerve Fiber Layer (NFL), the Ganglion Cell Layer (GCL), and the Inner Plexiform Layer (IPL), herein termed NGI. Maintenance of NGI structure correlates with RGC health (Bai et al., 2010a).

Figure 2:
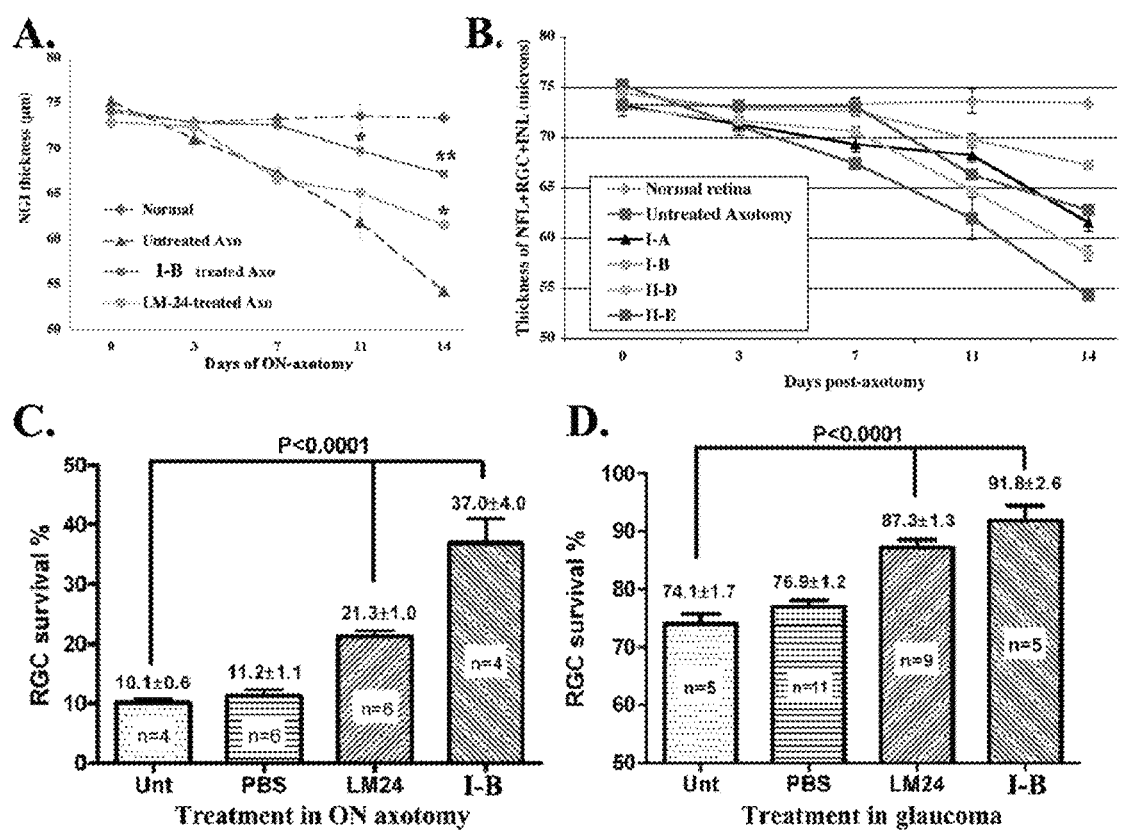
FIG. 2 shows that I-B and other novel compounds described herein inhibit retinal thinning and degeneration during disease, protect retinal structure, and delay RGC death. In (A) the thickness of the RGC and NFL (containing RGC soma, fibers and axons) was measured by FD-OCT, as described (Bai et al., 2010a). I-B significantly prevented thinning of the retinal layers. Each time point is the average of 3 individual rats measured over time ±sem, and in each rat the left eye is the normal untreated control. **p<0.01, *p<0.05. (B) shows that the novel compounds I-A, I-B, II-D, and II-E also prevent thinning of the NGI after axotomy. Two examples for "class I" (see Formula I) compounds I-A and I-B, and two examples for "class II" (see Formula II) compounds II-D and II-E are shown. (C) and (D) show that the p75 antagonists I-B and LM-24 significantly prevent the death of RGCs in ON axotomy (C) and glaucoma (D). In ON axotomy intravitreal injections of the indicated agents were done once immediately after ON transection and the endpoint was at day 14. In glaucoma intravitreal injections of the indicated agents were done at days 14 and 21 and the endpoint was at day 42. Data are % RGC survival ±sem, of the indicated (n) number of rats. The RGC density in the untreated contralateral normal eye is 100%.

In vivo treatment with I-B and LM-24 (3 µg dose immediately after ON axotomy) delayed the loss of retinal structure. I-B provided significant preservation of the NGI thickness, p<0.01 compared to untreated axotomy at days 11 and 14. In contrast, LM-24 provided very limited preservation of the NGI thickness and only at day 14, p<0.05 compared to untreated axotomy (FIG. 2A). Compound I-B had significantly better efficacy than LM-24 in protecting NGI thickness, especially early after injury (p<0.05 comparing I-B versus LM-24 at day 11 of ON axotomy) (FIG. 2A).

Similar results of neuronal protection were obtained in experiments carried out with inhibitors I-A, II-D, and II-E (FIG. 2B). Therefore, two examples for "class I" (see Formula I) compounds I-A and I-B, and two examples for "class II" (see Formula II) compounds II-D and II-E have been demonstrated.

Antagonists of p75NTR Prevent RGC Degeneration in Axotomy and Glaucoma

Quantification of surviving RGCs (fluorogold labeled) after 14 days of ON axotomy shows that treatment with I-B resulted in 37% RGCs surviving, and treatment with LM-24 resulted in lower surviving RGC, at 21%. This difference is significant p<0.0001, compared to the control axotomy group that had 10% RGCs surviving after 14 days (FIG. 2C). Compound I-B had significantly better efficacy than LM-24 in rescuing RGCs from death after ON axotomy (p<0.05 comparing I-B versus LM-24 at the endpoint).

In glaucoma, treatment with I-B was done at days 14 and 21 of stress, and quantification of surviving RGCs was at day 42 of glaucoma. Experimental eyes experienced constant high IOP throughout (data not shown). I-B treatment resulted in 92% RGCs surviving. This result was significant (p<0.0001), compared to the control glaucoma groups where 74-77% RGCs survived (FIG. 2D).

p75NTR Inhibitors Abolish a Paracrine Mechanism of RGC Death

In the retina p75NTR is also expressed in glia cells, which are known to secrete neurotoxic factors such as TNF-α and α2M. Thus, we tested whether p75NTR inhibitors can suppress secretion of neurotoxic factors.

Figure 3:
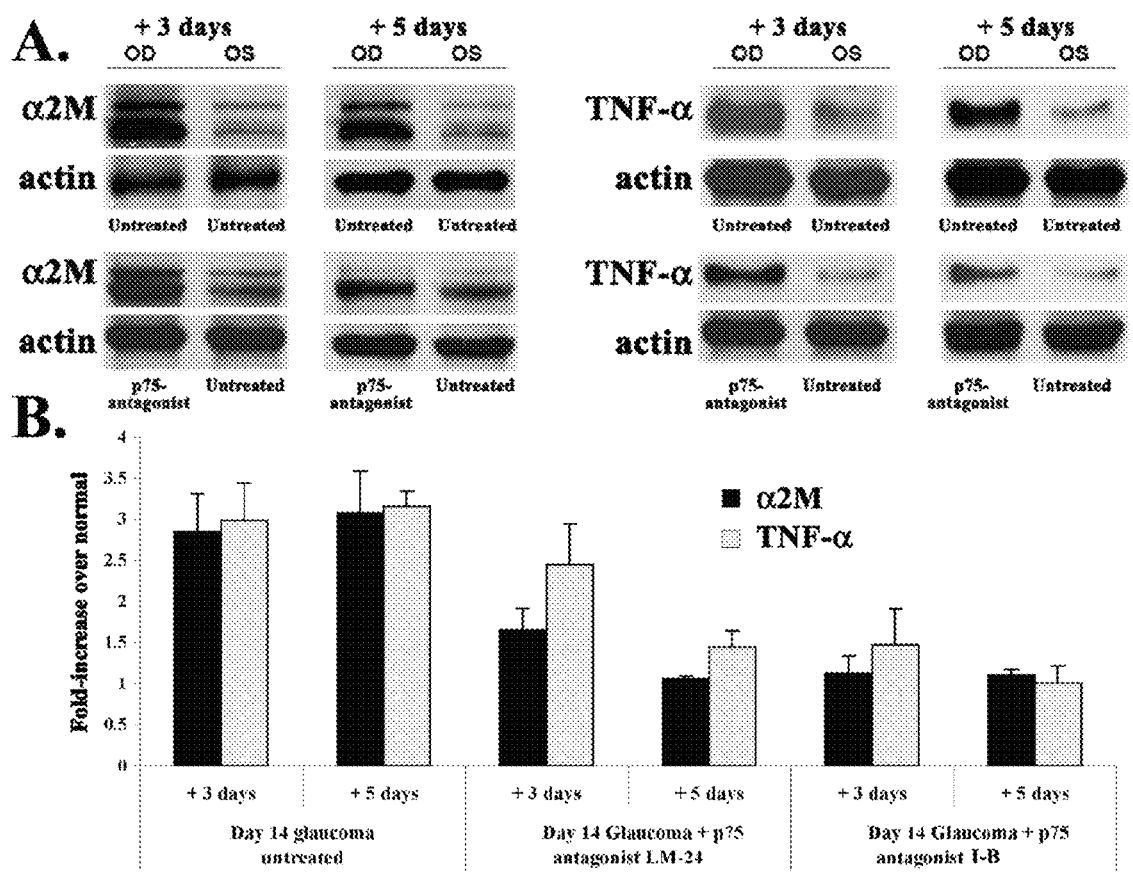
FIG. 3 shows that production of neurotoxic proteins α2M and TNF-α are exacerbated by a p75 agonist and are inhibited by p75 antagonists. In (A) Day 14 glaucomatous eyes (OD, right eyes) were untreated or were injected intravitreally with p75 antagonist I-B. Naïve contralateral eyes (OS, left eyes) were untreated controls. Three days or five days after injection (e.g. glaucoma day 17 or day 19) detergent extracts from the retinas were studied by western blotting for α2M and TNF-α, standardized versus actin loading control. Representative data from three assays using retinas was processed independently. (B) shows quantification of the fold-change in α2M and TNF-α, compared versus control normal retinas. Each time point is the average from 3 independent assays ±sem. The p75 antagonist I-B causes a time-dependent inhibition of the α2M and TNF-α that are up-regulated during glaucoma.

After 14-days of glaucoma eyes were injected intravitreally with p75NTR antagonists, and the levels of TNF-α and α2M were measured three days later (e.g. day 17 of glaucoma) and five days later (e.g. day 19 of glaucoma) (FIG. 3A).

The levels of both neurotoxic factors were reduced three days after injection of p75NTR antagonists, and were nearly normalized five days after injection of p75NTR antagonists (quantification in FIG. 3B). This result is remarkable given that the glaucomatous eyes endured constant high IOP (measured IOP data not shown).

These results demonstrate that in glaucoma RGC death is caused by the p75NTR-dependent up-regulation of TNF-α and α2M production. This increase in neurotoxins is reversible by p75 antagonists.

In summary, we report herein studies of the function of the TrkA and $p75^{NTR}$ receptors and of endogenous NGF in normal retinas and in retinas stressed chronically (glaucoma) or acutely (ON axotomy). We used pharmacological probes that target both receptors (wild type NGF), a selective agonist of TrkA (NGF mutant NGF-C), a selective agonist of $p75^{NTR}$ (NGF mutant NGF-A), a biological response modifier that blocks endogenous NGF and pro-NGF from binding to $p75^{NTR}$ (anti-NGF mAb NGF30); and small molecule antagonists of $p75^{NTR}$ (e.g., compound I-B).

We demonstrate herein that α2M binds to NGF and neutralizes NGF's neuroprotective action. The $p75^{NTR}$ selective ligand NGF-A induces RGC death in the normal retina, and accelerates RGC death in diseased eyes. Further, a biological response modifier that blocks endogenous NGF and pro-NGF (mAb NGF30) affords protection to RGCs during disease. These data demonstrate that endogenous NGF is bioavailable and capable of neuroprotection, provided its engagement to $p75^{NTR}$ is blocked. The data also show that selective agonists of TrkA (e.g. NGF-C) protect RGCs in chronic and in acute neurodegeneration.

The glaucoma and ON axotomy models of neurodegeneration are intrinsically different. Glaucoma is a slow, chronic and progressive disorder, and elevated IOP creates an intraocular crisis that exerts stress on each layer of the retina. In contrast, optic nerve transection is an acute disorder, where the problem is extraocular because it damages RGC axons and only in late stages affects the RGC cell body. In spite of their differences, both axotomized and glaucomatous retinas up-regulate regulate NGF, TrkA, and p75$^{NTR}$ (Cui et al., 2002; Hu et al., 1998; Lebrun-Julien et al., 2009b; Rudzinski et al., 2004). Our findings show that p75$^{NTR}$ antagonists (e.g., I-B) were effective at protecting RGCs in both chronic and acute neurodegeneration, and support the importance of p75$^{NTR}$ antagonism for promoting survival.

Thus, our results suggest that antagonism of p75$^{NTR}$ can prevent neurotoxicity, and that p75$^{NTR}$ antagonists can be used for prevention or treatment of neurodegeneration, for example in glaucoma and related forms of neuropathy or axonopathy. Our data validate p75$^{NTR}$ antagonists as candidate therapeutics for such disorders.

Experimental Procedures
Biology
Animals

Wistar rats (female, 250-300 g; Charles River) were kept in a 12 hours dark-light cycle with food and water ad libitum. All animal manipulations were performed between 9 AM and 12 AM. Deep anesthesia was used during cauterization (induction of glaucoma), ON transection, fluorogold labeling, intraocular injection procedures, Optical Coherence Tomography measurements, and euthanasia (ketamine, xylazine, acepromazine injected intraperitoneally: 50/5/1 mg/kg, as per IACUC recommendations). For measuring IOP, light anesthesia was used (a gas mixture of Oxygen, 2% isofluorane mixture, at a rate of 2.5 liter/min, as per IACUC recommendations).

Glaucoma Model and Intraocular Pressure

The episcleral vein cauterization (EVC) model of rat (Shi et al., 2007; Shi et al., 2008) was used. In the glaucoma model ~1.7-fold elevated intraocular pressure (IOP) was maintained for as long as 4 months (data not shown).

Optic Nerve Transection

The ON axotomy model in the rat (Bai et al., 2010a) was used. The ON was exposed and was completely transected 0.5-1.0 mm posterior to the eyeball with the use of microtweezers, sparing vessels. Normal blood circulation in the retina was ascertained.

Intravitreal Injections

The experimental eyes were injected with test or control vehicle while the contralateral eyes served as naive normal controls.

Fluorogold Retrograde Labeling

RGCs were retrogradely labeled with a 4% Fluorogold solution (Fluorochrome, Englewood, Colo.) applied bilaterally to the superior culliculous (SC) (Bai et al., 2010a).

Quantification of Retinal Structures Using Fourier Domain Optical Coherence Tomography (FD-OCT)

FD-OCT is a non-invasive method that allows time-kinetic studies in the same animal. Details of the method have been published (Bai et al., 2010a). During retinal scanning, three volumes were acquired in different sectors of the retina containing the ON head and retinal blood vessels as landmarks. In post processing, six B-scans were randomly selected from each volume. The retinal thickness measurements were performed with ImageJ software. In each B-scan the thickness of the NFL-GCL-IPL (NGI) was measured at four adjacent points at a distance 1.5 mm from the ON head.

Drug Treatments

Drug treatments were done with the experimenters blinded to treatment code. In each rat we used one experimental eye (right eye, OD) with or without treatment, and the naïve contralateral eyes (left eye, OS) were always normal and untreated and were standardized to 100% RGCs.

Drug Regimen In Vivo

In all cases, the vehicle and drugs were coded and the experimenters were masked to the treatment (double-blinded studies). Codes were broken upon deposit of a summary of the data. All intravitreal injections delivered 3 μl. For proteins 1.0 μg was injected from wild type NGF stock (12 μM). For small molecules a total dose of 3.0 μg was injected (LM-24 (3.0 mM stock), I-B (3.0 mM stock)). PBS was the vehicle control.

For studies in the glaucoma animal model the injections were performed at days 14 and 21 after cauterization. The endpoint was at day 42 of high IOP. Thus, in this paradigm there is pre-existing damage for 14 days before treatment (measured at ~8% RGC death (Shi et al., 2007; Shi et al., 2008)); and the treatments require long-lived efficacy in the constant presence of retinal stress due to high IOP. For studies in the ON axotomy animal model the injections were performed immediately after the ON transection (while the rat was still under general anesthesia). For testing a higher frequency of wild type NGF, this reagent was administered immediately after ON transection and also at 7 days after optic nerve transection (2× treatment). The endpoint was at day 7 or day 14 after ON sectioning, as indicated.

Binding Assays with p75NTR Small Molecule Antagonists

The compound LM-24 has been reported by others (Massa et al., 2006). Binding studies were carried out with all the compounds using I-B as reference.

Competitive ELISA Assays

Competitive ELISAs were performed as described (Saragovi et al., 1998). The procedure immobilized 50 ng/well NGF, or pro-NGF (Alomone Labs, Israel) onto polystyrene 96-well microtest plates, with washing and blocking with binding buffer (BB; phosphate buffered saline containing 0.5% bovine serum albumin). The following primary reagents in BB were added: recombinant chimeric p75-Fc or recombinant chimeric TrkA-Fc (R&D), or anti-NGF mAb NGF30 (Saragovi et al., 1998); each at 50 nM. The competitors I-B and the other test compounds (or control LM-24) were added at the indicated concentrations, and the plates were incubated for 45 minutes. After washing 3× in BB, HRP-conjugated secondary reagents (Sigma) were added for 30 min (goat anti-human Fc for p75-Fc and for TrkA-Fc; and goat anti-rat Ab for NGF30 mAb), and then wells were washed 3× in BB and 1× in PBS. Peroxidase activity was determined colorimetrically using the substrate TMB One Solution (Promega). The reaction was stopped with 0.5 N $H_2SO_4$ and the plates were read at 450 nm (Benchmark Plus, Bio-Rad). Assays were repeated n>4 times, with replicates of 4 wells each assay. Wells that received either vehicle, inactive compounds, or no competitor served as controls and were standardized as 100% binding. Wells with no NGF immobilized but with all other reagents added were treated as background (<15% of maximal signals) and standardized to 0% binding.

Quantification of RGCs Survival

Quantification of labeled RGCs was performed as reported (Shi et al., 2007; Shi et al., 2008). At the end-point of each experiment, both eyes were enucleated and isolated retinas were flat-mounted on a glass slide with the vitreous side up. Pictures for each freshly flat-mounted retina were taken using a Zeiss fluorescence microscope (Carl Zeiss Meditec, Jena, Germany), with 12 pictures/retina at 20× magnification. For each quadrant there were 3 pictures (at a radial distance of 1 mm, 2 mm, 3 mm from the optic nerve). In all cases, manual RGC counting was performed by two independent persons. One person was the experimental performer, masked to drug treatment code, the second person was unrelated to the experiment and was masked to the whole protocol. Also, automated quantitative counting was done with "Metamorph" software (Molecular Devices) using the module "Count Nuclei" to identify cells as unique objects. The selected parameters for retinal ganglion cells were 8-15 µM for the width range. Both manual counts and the automated counts were generally in accordance, and deviations amongst them were <5% per picture.

Statistical Analysis of RGC Survival

In each rat standardization of % RGCs survival was calculated as the ratio of the experimental eye versus contralateral normal control eye (RGCexperimental/RGCcontralateral*100%; OD/OS). The % RGCs survival for each experimental group (untreated, PBS, NGF-wild type, NGF mutants) were averaged ±sem; the number (n) of ratios is indicated in each graph and legend. For IOP data, FD-OCT data, and RGCs counting data, the mean±sem are shown. After quantification of Western blot data, the mean±SD are shown. Data analysis was performed using GraphPad Prizm 5 software (GraphPad Software Inc., San Diego, Calif.). Comparison between the RGCs survival rate is using one-way ANOVA with Dunnett's multiple comparison test. For IOP and FD-OCT results, the data were analyzed by Repeated Measures ANOVA with SPSS 13.0 software followed by post-hoc tests (Tukey HSD) for comparisons among the groups.

Quantification of TNF-α and α2-Macroglobulin Expression

Both retinas of each animal were detergent solubilized, and studied in independent gels standardized to loading control. The ratio of the glaucoma eye ±treatment versus the normal contralateral eye was calculated, and results were averaged ±sem, n=3 animals per group. In glaucoma, all drug treatments were done at day 14 of hypertension. In one group the retinas were harvested at day 17 of glaucoma (3 days after intraocular injection) and in the other group the retinas were harvested at day 19 of glaucoma (5 days after intraocular injection). Normal eyes treated with NGF-A were collected in the indicated days. After SDS-PAGE and western transfer, membranes were immunoblotted with rabbit polyclonal antibodies against TNF-α (Preprotech) or α2M (Santa Cruz) at a 1:3000 dilution. Goat anti-rabbit secondary antibodies conjugated to horseradish peroxidase (Sigma) were used at a 1:10,000 dilution. Loading was controlled with antibodies to β-actin (Sigma). For digital quantification, membranes were scanned and analyzed using ImageJ software.

Bioassays. Pro-NTF Killing Assay.

The cell lines B104 (expressing ~50,000 p75NTR/cell) and nnr5 (expressing ~150,000 p75NTR/cell) do not express detectable TrkA, and do not respond to NGF (Maliartchouk et al., 2000). Cells (5,000 cells/well) were cultured in 96-well plates (Falcon, Lincoln Park, N.J.) in normal culture media (RPMI1640, Hepes, Glutamine, 5% serum). Wells were supplemented with NGF, BDNF, pro-NGF, or pro-BDNF (Alomone Labs) (50 nM final), in the presence or absence of I-B (20 µM final). Wells containing all culture conditions but no cells were used as blanks. The growth/survival profile of the cells was quantified using MTT (Sigma) 72 hours after plating. Optical density readings of MTT were done in a Benchmark Plus microplate Spectrophotometer (BioRad) at 595 nm with blanks subtracted.

Synthetic Chemistry

The following organic solvents (ACS grade) were obtained from Sigma-Aldrich Corp. (St. Louis, Mo., United States of America): dimethyl sulfoxide, ethyl acetate, petroleum ether (b.p. 35-60° C.), DMF, chloroform. Methanol (ACS) was purchased from Fisher and acetonitrile (HPLC grade) was ordered from EMD. The reagents 3,3,3-trifluoropropan-1-amine and 4,4,4-trifluorobutan-1-amine were obtained from SynQuest Inc, theophylline-7-acetic acid was from AK Scientific Inc, DIC was from ACT and sodium bicarbonate, Pd 10% wt on activated carbon, Celite, DCC, EEDQ, N-hydroxysuccinimide, benzyl N-(3-hydroxypropyl)carbamate and 1,3-di-p-tolylcarbodiimide were purchased from Aldrich. Deuterated chloroform ($CDCl_3$) was delivered from Cambridge Isotopes Lab Inc, and deuterated dimethylsulfoxide (d6) was from ISOTEC Inc.

Flash chromatography was performed using Silica Gel 60A 230-400 mesh (ACP Chemicals).

Analytical thin layer chromatography (TLC) was done on aluminum-backed silica plates coated with a 0.2-mm thickness of Silica Gel 60 F254 (Aldrich) and visualized by UV irradiation and/or iodine.

Electrospray ionization (ESI) mass spectrometry (Agilent) was performed by the Centre regional de spectroscopie de masse de l'Université de Montreal. 1H NMR spectra were recorded on Varian 300 MHz and Bruker 300 MHz spectrometers.

Synthetic Example 1

Synthesis of Th53 (I-A)

2-(1,3-dimethyl-2,6-dioxo-2,3-dihydro-1H-purin-7(6H)-yl)-N-(4,4,4-trifluorobutyl)acetamide 1 mmol from theophylline-7-acetic acid (238 mg) and 4,4,4-trifluorobutan-1-amine (127 mg) was dissolved in 3 ml of DMSO. An equimolar amount of N,N'-dicyclohexylcarbodiimide (206 mg) was added and the solution was stirred for 48 h at ambient temperature. The solvent was filtered and concentrated under high vacuum. The oily residue, dissolved in minimal amount of ethyl acetate was subjected to flash chromatography. The following eluents were used: ethyl acetate: petroleum ether (2:1), ethyl acetate and ethyl acetate:methanol (9:1). The fractions containing the new spot (Rf=0.07, TLC, ethyl acetate) were collected and evaporated. The white powder was recrystallized from ethyl acetate/petroleum ether.

M.p. 181-184° C. Yield: 69 mg (20%). The molecular mass of the product was analyzed by LC/MS (Agilent) and was found to be 348 $(M+H)^+$, thus confirming the suggested structure of F.W. 347. 1H-NMR Spectrum (300 MHz) was consistent with the expected structure.

Synthetic Example 2

Synthesis of Th69 (I-B)

1,3-Diisopropyl-1-[2-(1,3-dimethyl-2,6-dioxo-1,2,3,6-tetrahydro-purin-7-yl)-acetyl]-urea (ThAc-N-DIU) was synthesized as follows A solution of 119 mg (0.5 mmol) theophylline-7-acetic acid in 5 ml DMF was dropped for 15-20 minutes into preheated at 60° C. solution of 80 µl N,N'-diisopropyl carbodiimide (DIC) in 2.5 ml DMF. The mixture was subsequently heated for 4 hours at the same temperature. After cooling the solvent was evaporated in a vacuum. The residue was dissolved in minimal amount of chloroform and purified by flash chromatography on Silicagel-60A with chloroform:methanol (98:2) as eluent. The fractions with the desired product were pooled and evaporated, yielding 82 mg (44%) from the compound Th69 as a white powder. Rf=0.68 (chloroform/methanol (9/1), Rf=0.23 (ethyl acetate). The empirical formula (F.W. 365) was confirmed by the results from LC/MS. The main molecular peak was found at 365 with a second peak at 387 for the sodium salt. The m.p. of the product was 117-120° C. The 1H-NMR Spectrum (300 MHz) was consistent with the expected structure.

Synthetic Example 3

Synthesis of Th60 (II-D)

3'-Aminopropyl (1,3-dimethyl-2,6-dioxo-2,3-dihydro-1H-purin-7(6H)-yl)acetate was synthesized as follows To 60 mg of Th56 dissolved in 7 ml of methanol was added 30 mg of Palladium 10% on activated carbon suspended in 7 ml of the same solvent. The mixture was stirred for 3 hours at room temperature under hydrogen. The suspension was filtered over Celite, washed with methanol and evaporated. The purification was performed with flash column chromatography using chloroform and methanol with increasing polarity. The fractions containing the second spot (Rf=0.32, C/M=7/1) were pooled and evaporated.

Synthetic Example 4

Synthesis of Th56 (II-E)

3'-(Benzyloxycarbonylamino)propyl (1,3-dimethyl-2,6-dioxo-2,3-dihydro-1H-purin-7(6H)-yl)acetate was synthesized as follows The carboxyl function of theophylline-7-acetic acid (119 mg, 0.5 mmol) was activated by the addition of N-hydroxysuccinimide (57.5 mg, 0.5 mM) and EEDQ (127 mg, 0.5 mmol) in 4 ml dry DMF for 1 hour at room temperature. To this solution was added dropwise 107 mg (0.5 mmol) benzyl N-(3-hydroxypropyl)carbamate and the reaction mixture was stirred for 24 hours. The solvent was removed under vacuum; the product was dissolved in chloroform and purified by flash chromatography on Silicagel-60A with ethyl acetate/petroleum ether used as eluents. The fractions from the third spot (Rf=0.32, ethyl acetate) were pooled, concentrated and washed with 1N sodium bicarbonate. After evaporation of the organic solvent, 54 mg (25%) from Th56 were isolated. The observed mass by LC/MS was 430 for [M+H]$^+$, corresponding to the expected mass of 429.

Synthetic Example 5

Synthesis of Th70-2 (I-F)

2-(1,3-dimethyl-2,6-dioxo-2,3-dihydro-1H-purin-7(6H)-yl)-N-(3,3,3-trifluoropropyl)acetamide was synthesized as follows This compound was obtained from 3,3,3-trifluoropropan-1-amine by a procedure similar to that which was used for the preparation of compound I-A. The product was purified by chromatography on a silica gel column eluted with ethyl acetate. TLC: Rf=0.07, ethyl acetate. After recrystallization from ethyl acetate/petroleum ether, the white powder had m.p. 203-206° C. The LC/MS (F.W. 333) was found 344 (M+H)$^+$, thus confirming the suggested structure. The 1H-NMR Spectrum (300 MHz) was consistent with the expected structure.

Synthetic Example 6

Synthesis of Th92 (I-Q)

2-(1H-indol-3-yl)-N-isopropyl-N-(isopropylcarbamoyl)acetamide

To 87.5 mg (0.5 mM) of 3-indolylacetic acid dissolved in dry DMF was added 79 ul (0.5 mM) N,N'-diisopropyl carbodiimide and the mixture was stirred overnight at RT. The solvent was evaporated, the residue was triturated with dry diethyl ether and the crystals formed from DIU were filtered. The flash chromatography from $CHCl_3$ and $CHCl_3$/MeOH 99/1 yielded 91 mg light yellow oil (60%) with Rf=0.82 ($CHCl_3$/MeOH 9/1). The observed mass by LC/MS was 302 for [M+H]$^+$, corresponding to the expected mass of 301.

Synthetic Example 7

Synthesis of Th93 (I-R)

3-(1H-indol-3-yl)-N-isopropyl-N-(isopropylcarbamoyl) propanamide was synthesized and purified similarly to Synthetic Example 6. The main product was collected in fractions 32-43 and after pooling and evaporation 83 mg (53%) of oily product was isolated. Rf=0.61 ($CHCl_3$/MeOH 95/5). The LC/MS (F.W. 315) was found to be 316 (M+H)$^+$.

Synthetic Example 8

Synthesis of Th95 (I-S)

3-(1H-indol-3-yl)-N-p-tolyl-N-(p-tolylcarbamoyl) propanamide was synthesized as follows 111 mg (0.5 mmol) of 1,3-di-p-tolylcarbodiimide was dissolved in 1 ml DMF and activated by heating for 2 hours at 60° C. (oil bath). 94 mg (0.5 mmol) of 3-indolylacetic acid, dissolved in dry DMF was added to the solution and the mixture was heated and stirred for another 3 hours at 60° C. The solvent was evaporated under high vacuum and the residue was recrystallized from ethyl acetate/petroleum ether. The melting point of the crystals was 162-164° C. Rf=0.67 ($CHCl_3$/MeOH 98/2). The main molecular peak was found at 412 (F.W.=411.5) with a second peak at 434 for the sodium salt.

Synthetic Example 9

Synthesis of Th86 (II-N)

Methyl 2-(2,6-dioxo-1,3-dipropyl-2,3-dihydro-1H-purin-7(6H)-yl)acetate was prepared as follows A stirred suspension of 118 mg (0.5 mmol) 1,3-dipropylxanthine and anhydrous 69 mg $K_2CO_3$ (0.5 mmol) in 1 ml DMF was brought to 70° C. for 1 hour. Then methyl chloroacetate (48 ul, 0.55 mmol) was added dropwise and the mixture was stirred for 2 hours at 65° C. The solution was cooled to room temperature and water was added, yielding 85 mg (55%) of micro needles. Rf=0.56 (ethyl acetate). The empirical formula (F.W. 308) was confirmed by the results from LC/MS. The main molecular peak (M+H)+ was found at 309. The melting point of the product was 77-79° C.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The contents of all documents and references cited herein are hereby incorporated by reference in their entirety.

This application claims priority to U.S. application No. 61/392,647, filed Oct. 13, 2010, the entire contents of which are hereby incorporated by reference.

ABBREVIATIONS AND CODES

| | | |
|---|---|---|
| I-A | Th53 | ThAcN(CH$_2$)$_3$CF$_3$ |
| I-B | Th69 | ThAc-NDIU |
| I-F | Th70-2 | ThAcN(CH$_2$)$_2$CF$_3$ |
| I-G | Th41 | ThAc-NDCU |
| I-Q | Th92 | 3-IndAc-NDIU |
| I-R | Th93 | 3-IndPr-NDIU |
| I-S | Th95 | 3-IndPr-NDTU |
| II-D | Th60 | ThAcO(CH$_2$)$_3$NH$_2$ |
| II-E | Th56 | ThAcO(CH$_2$)$_3$NH-Z |
| II-H | Th75 | ThAcOMe |
| II-N | Th86 | Di-Pr-Xanth-AcOMe |

TABLE OF ABBREVIATIONS

| | |
|---|---|
| ALS | amyotrophic lateral sclerosis |
| BDNF | brain derived neurotrophic factor |
| C | chloroform |
| d | day |
| DCC | 1,3-dicyclohexyl carbodiimide |
| DCU | -1,3-dicyclohexyl ureide |
| DIC | N,N'-diisopropyl carbodiimide |
| DIU | -1,3-diisoporpyl ureide |
| DMF | N,N-dimethyl formamide |
| DMSO | dimethyl sulfoxide |
| DTU | -1,3-di-p-tolyl ureide |
| EA | ethyl acetate |
| EEDQ | N-Ethoxycarbonyl-2-ethoxy-1,2-dihydroquinoline |
| ELISA | Enzyme Linked ImmunoSorbent Assay |
| ESI | Electrospray Ionization |
| EVC | Episcleral vein cauterization |
| F.W. | formula weight |
| g | gram |
| h | hour |
| HEPES | 4-2-hydroxyethyl-1-piperazine ethanesulfonic acid |
| HPLC | high-pressure liquid chromatography |
| HRP | horseradish peroxidase |
| IOP | intraocular pressure |
| i.p. | Intraperitoneal |
| i.v. | intravenous |
| IgG | Immunoglobulin G |
| kg | kilogram |
| LC/MS | liquid chromatography-mass spectrometry |
| µg | microgram |
| µl | microliter |
| µM | micromolar |
| M | methanol |
| M.p. | melting point |
| mg | milligram |
| min | minute |
| ml | milliliter |
| mM | millimolar |

TABLE OF ABBREVIATIONS-continued

| | |
|---|---|
| mol | mole |
| MTT | 3-(4,5-dimethylthiazol-2-yl)-2,5-diphenyltetrazolium bromide |
| MW | molecular weight |
| NaCl | sodium chloride |
| ng | nanogram |
| NGF | nerve growth factor |
| nM | nanomolar |
| NMR | nuclear magnetic resonance |
| NS | not significant |
| NT-3 | neurotrophin-3 |
| NT-4/5 | neurotrophins-4 and -5 |
| ON | optic nerve |
| p75$^{NTR}$ | neutrophin receptor |
| PBS | phosphate buffered saline |
| pM | picomol |
| RGC | retina ganglion cell |
| RT | retention time |
| SDS | sodium dodecyl sulphate |
| SE | standard error |
| TFA | trifluoroacetic acid |
| TLC | thin layer chromatography |
| TNF | tumor necrosis factor |
| TRIS | 2-Amino-2-hydroxymethyl-propane-1,3-diol |
| Trk A | tropomyosin-related kinase A |
| Z | benzyloxycarbonyl residue |

REFERENCES

Bai, Y., Jing Xu, Fouad Brahimi, Yehong Zhuo, Marinko V. Sarunic, and Saragovi, H. U. (2010a). An agonistic anti-TrkB mAb, but not BDNF, causes sustained TrkB activation, delays RGC death, and protects the retinal structure in optic nerve axotomy and in glaucoma. Invest Ophthalmol Vis Sci 51, 4722-4731.

Bai, Y., Shi, Z., Zhuo, Y., Liu, J., Malakhov, A., Ko, E., Burgess, K., Schaefer, H., Esteban, P. F., Tessarollo, L., and Saragovi, H. U. (2010b). In glaucoma the up-regulated truncated TrkC.T1 receptor isoform in glia causes increased TNF-{alpha} production, leading to retinal ganglion cell death. Invest Ophthalmol Vis Sci.

Cui, Q., Tang, L. S., Hu, B., So, K. F., and Yip, H. K. (2002). Expression of trkA, trkB, and trkC in injured and regenerating retinal ganglion cells of adult rats. Invest Ophthalmol Vis Sci 43, 1954-1964.

Hu, B., Yip, H. K., and So, K. F. (1998). Localization of p75 neurotrophin receptor in the retina of the adult SD rat: an immunocytochemical study at light and electron microscopic levels. Glia 24, 187-197.

Klosa, J. (1955). [Reactivity of the 7 position of theophylline. II. Synthesis of theophylline derivatives.]. Archiv der Pharmazie and Berichte der Deutschen Pharmazeutischen Gesellschaft 288, 301-303.

Lebrun-Julien, F., Bertrand, M. J., De Backer, O., Stellwagen, D., Morales, C. R., Di Polo, A., and Barker, P. A. (2010). ProNGF induces TNFalpha-dependent death of retinal ganglion cells through a p75NTR non-cell-autonomous signaling pathway. Proc Natl Acad Sci USA 107, 3817-3822.

Lebrun-Julien, F., Duplan, L., Pernet, V., Osswald, I., Sapieha, P., Bourgeois, P., Dickson, K., Bowie, D., Barker, P. A., and Di Polo, A. (2009a). Excitotoxic death of retinal neurons in vivo occurs via a non-cell-autonomous mechanism. J Neurosci 29, 5536-5545.

Lebrun-Julien, F., Morquette, B., Douillette, A., Saragovi, H. U., and Di Polo, A. (2009b). Inhibition of p75(NTR) in glia potentiates TrkA-mediated survival of injured retinal ganglion cells. Mol Cell Neurosci 40, 410-420.

Maliartchouk, S., Debeir, T., Beglova, N., Cuello, A. C., Gehring, K., and Saragovi, H. U. (2000). Genuine monovalent ligands of TrkA nerve growth factor receptors reveal a novel pharmacological mechanism of action. J Biol Chem 275, 9946-9956.

Massa, S. M., Xie, Y., Yang, T., Harrington, A. W., Kim, M. L., Yoon, S. O., Kraemer, R., Moore, L. A., Hempstead, B. L., and Longo, F. M. (2006). Small, nonpeptide p75NTR ligands induce survival signaling and inhibit proNGF-induced death. J Neurosci 26, 5288-5300.

Nakazawa, T., Nakazawa, C., Matsubara, A., Noda, K., Hisatomi, T., She, H., Michaud, N., Hafezi-Moghadam, A., Miller, J. W., and Benowitz, L. I. (2006). Tumor necrosis factor-alpha mediates oligodendrocyte death and delayed retinal ganglion cell loss in a mouse model of glaucoma. J Neurosci 26, 12633-12641.

Peikov, P., Danchev, N., Zlatkov, A., Ivanov, D., and Belcheva, N. (1995). Synthesis, toxicological, pharmacological, and bronchodilating activity in vitro of some xanthineacetic acid derivatives. Archiv der Pharmazie 328, 615-618.

Rudzinski, M., Wong, T. P., and Saragovi, H. U. (2004). Changes in retinal expression of neurotrophins and neurotrophin receptors induced by ocular hypertension. J Neurobiol 58, 341-354.

Saragovi, H. U., Zheng, W., Maliartchouk, S., DiGugliemo, G. M., Mawal, Y. R., Kamen, A., Woo, S. B., Cuello, A. C., Debeir, T., and Neet, K. E. (1998). A TrkA-selective, Fast Internalizing Nerve Growth Factor-Antibody Complex Induces Trophic but Not Neuritogenic Signals. J. Biol. Chem. 273, 34933-34940.

Shi, Z., Birman, E., and Saragovi, H. U. (2007). Neurotrophic rationale in glaucoma: a TrkA agonist, but not NGF or a p75 antagonist, protects retinal ganglion cells in vivo. Dev Neurobiol 67, 884-894.

Shi, Z., Rudzinski, M., Meerovitch, K., Lebrun-Julien, F., Birman, E., Di Polo, A., and Saragovi, H. U. (2008). alpha 2 macroglobulin is a mediator of retinal ganglion cell death in glaucoma. J Biol Chem 283, 29156-29165.

Tezel, G., and Wax, M. B. (2004). The immune system and glaucoma. Curr Opin Ophthalmol 15, 80-84.

Wax, M. B., and Tezel, G. (2002). Neurobiology of glaucomatous optic neuropathy: diverse cellular events in neurodegeneration and neuroprotection. Mol Neurobiol 26, 45-55.

We claim:

1. A p75 receptor inhibitor of Formula I:

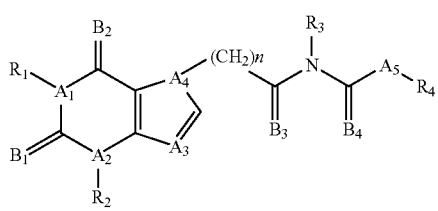

(I)

wherein:
$A_1, A_2, A_3$, and $A_4$ are each N;
$A_5$ is NH;
$B_1, B_2, B_3$ and $B_4$ are each independently selected from the group consisting of O and S;
$R_1$ and $R_2$ are each independently selected from the group consisting of H, alkyl, substituted alkyl, cycloalkyl, aryl, and substituted aryl;
$R_3$ and $R_4$ are each independently selected from the group consisting of alkyl, isoalkyl, aryl, aralkyl, hydroxyl, alkoxyl, hydroxyalkyl, hydroxycycloalkyl, alkoxycycloalkyl, aminoalkyl, acyloxyl, alkylaminoalkyl and alkoxycarbonyl; and
n is an integer from 0 to 8;
or a pharmaceutically acceptable salt thereof, said inhibitor having binding specificity for p75$^{NTR}$ receptor.

2. A p75 receptor inhibitor of structure (Ia):

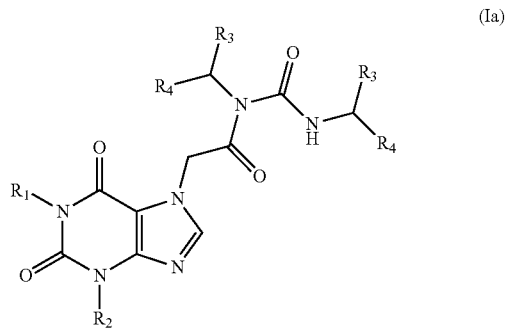

(Ia)

wherein:
$R_1$ and $R_2$ are each independently selected from the group consisting of H, alkyl, substituted alkyl, cycloalkyl, aryl, substituted aryl, aralkyl and aralkyloxyl; and
$R_3$ and $R_4$ are each independently selected from the group consisting of H, alkyl, isoalkyl, cycloalkyl, aryl, aralkyl, hydroxyl, alkoxyl, hydroxyalkyl, hydroxycycloalkyl, alkoxycycloalkyl, aminoalkyl, acyloxyl, alkylaminoalkyl and alkoxycarbonyl;
or a pharmaceutically acceptable salt thereof, said inhibitor having binding specificity for p75$^{NTR}$ receptor.

3. The p75 receptor inhibitor of claim 1, wherein the compound has the following structure (Ib):

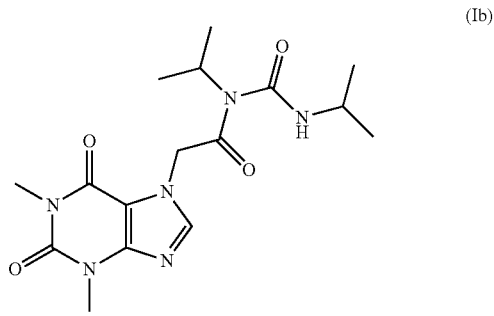 [SMILES: CC(C)NC(=O)N(C(=O)Cn1cnc2c1c(=O)n(C)c(=O)n2C)C(C)C]

(Ib)

or a pharmaceutically acceptable salt thereof.

4. A pharmaceutical composition comprising the p75 or inhibitor of claim 1 and a pharmaceutically acceptable carrier.

5. A method for inhibiting p75 receptor in a subject comprising administering the p75 receptor inhibit of claim 1 to the subject, such that p75 receptor is inhibited in said subject.

* * * * *